(12) United States Patent
Ho

(10) Patent No.: US 10,222,344 B2
(45) Date of Patent: Mar. 5, 2019

(54) GAS SENSOR

(71) Applicant: Winbond Electronics Corp., Taichung (TW)

(72) Inventor: Yu-Hsuan Ho, Taichung (TW)

(73) Assignee: Winbond Electronics Corp., Taichung (TW)

( * ) Notice: Subject to any disclaimer, the term of this patent is extended or adjusted under 35 U.S.C. 154(b) by 154 days.

(21) Appl. No.: 15/257,925

(22) Filed: Sep. 7, 2016

(65) Prior Publication Data

US 2017/0370863 A1  Dec. 28, 2017

(30) Foreign Application Priority Data

Jun. 23, 2016 (CN) .......................... 2016 1 0464098

(51) Int. Cl.
G01N 27/04 (2006.01)
G01N 27/12 (2006.01)
G01N 27/27 (2006.01)

(52) U.S. Cl.
CPC ............. *G01N 27/04* (2013.01); *G01N 27/12* (2013.01); *G01N 27/27* (2013.01)

(58) Field of Classification Search
CPC ......... G01N 27/04; G01N 27/27; G01N 27/12

USPC ......................................... 324/600, 691, 693
See application file for complete search history.

(56) References Cited

U.S. PATENT DOCUMENTS

| 3,879,717 A | * | 4/1975 | Gruensfelder | ....... | G08B 17/117 340/527 |
| 4,443,791 A | * | 4/1984 | Risgin | ..................... | G08B 29/24 340/634 |
| 6,489,787 B1 | * | 12/2002 | McFadden | ............. | G01N 27/16 324/656 |
| 6,801,060 B2 | | 10/2004 | Ikehashi et al. | | |
| 8,283,704 B2 | | 10/2012 | Tsukada | | |

* cited by examiner

Primary Examiner — Amy He
(74) Attorney, Agent, or Firm — JCIPRNET

(57) ABSTRACT

A gas sensor including a first sensing component, a second sensing component and a voltage enhancement circuit is provided. The first sensing component is coupled between a first voltage and a first node, where an impedance value of the first sensing component is proportional to a gas concentration. The second sensing component is coupled between the first node and a second voltage, where an impedance value of the second sensing component is inversely proportional to the gas concentration. The voltage enhancement circuit is coupled to the first node to receive a node voltage provided by the first node, and correspondingly provides a gas sensing voltage.

7 Claims, 1 Drawing Sheet

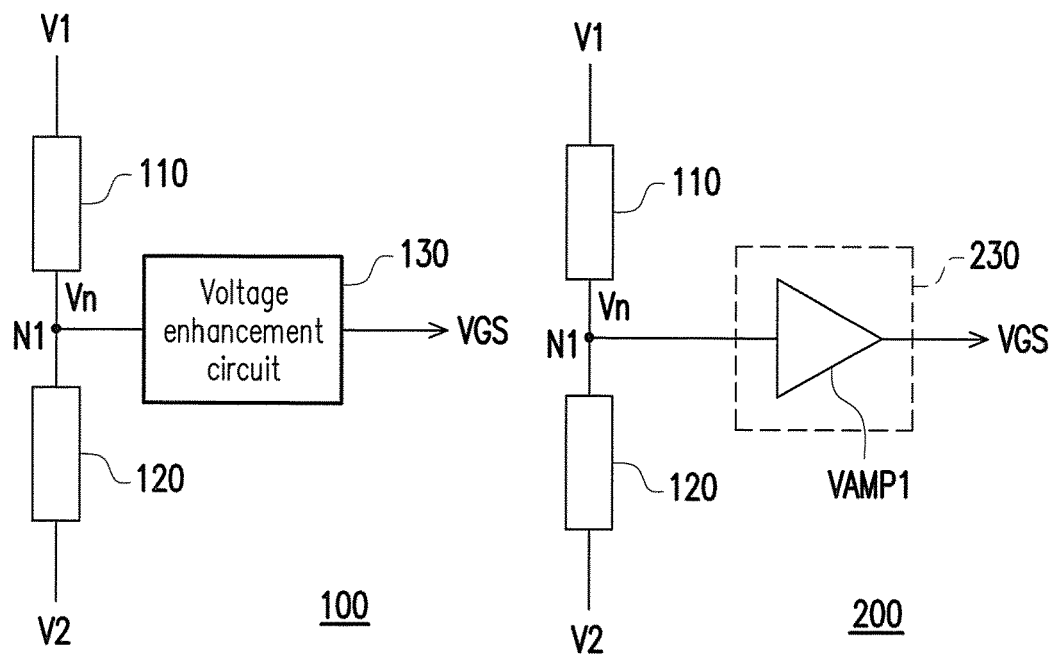
FIG. 1
FIG. 2
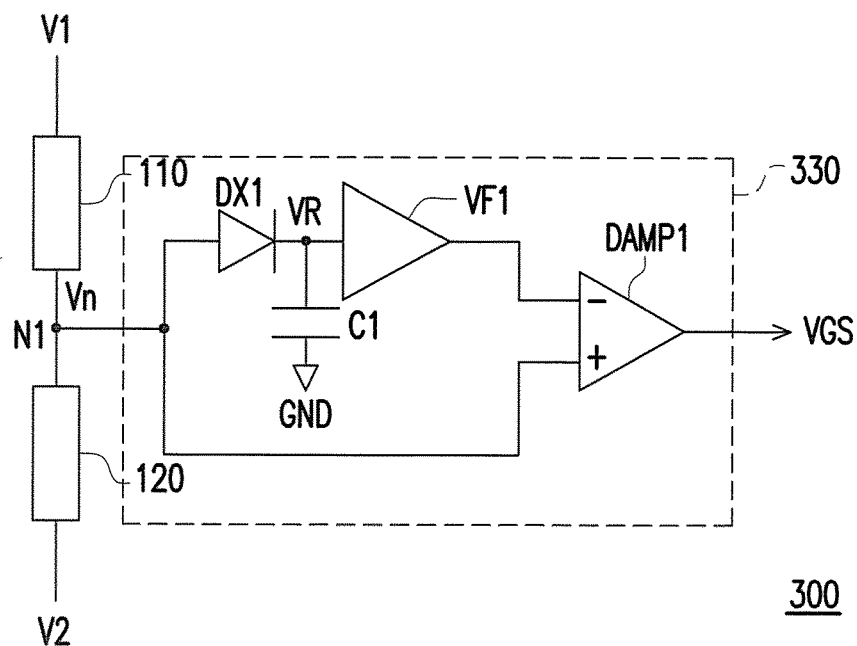
FIG. 3

US 10,222,344 B2

GAS SENSOR

CROSS-REFERENCE TO RELATED APPLICATION

This application claims the priority benefit of China application serial no. 201610464098.5, filed on Jun. 23, 2016. The entirety of the above-mentioned patent application is hereby incorporated by reference herein and made a part of this specification.

BACKGROUND OF THE INVENTION

Field of the Invention

The invention relates to a sensor, and particularly relates to a gas sensor.

Description of Related Art

Development of chemical industry and extensive use of internal-combustion engines (i.e. motor) cause serious environmental pollution, where air pollution has the most direct impact on human daily life. Therefore, along with today's increasing air pollution sources, it has been a trend to detect an abnormal state of the environment at anytime anyplace through a gas sensor. Therefore, how to improve accuracy of the gas sensor becomes an important issue.

SUMMARY OF THE INVENTION

The invention is directed to a gas sensor, which improves sensing sensitivity of a gas concentration.

The invention provides a gas sensor including a first sensing component, a second sensing component and a voltage enhancement circuit. The first sensing component is coupled between a first voltage and a first node, where an impedance value of the first sensing component is proportional to a gas concentration. The second sensing component is coupled between the first node and a second voltage, where an impedance value of the second sensing component is inversely proportional to the gas concentration. The voltage enhancement circuit is coupled to the first node to receive a node voltage provided by the first node, and correspondingly provides a gas sensing voltage.

According to the above description, the gas sensor of embodiments of the invention push-pull the node voltage of the first node according to the gas concentration through the first sensing component and the second sensing component connected in series and having positive and negative resistance coefficients, so that a variation amplitude of the node voltage can be increased relative to the gas concentration, i.e. sensing sensitivity for the gas concentration is improved.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 1 is a circuit schematic diagram of a gas sensor according to an embodiment of the invention.

FIG. 2 is a circuit schematic diagram of a gas sensor according to another embodiment of the invention.

FIG. 3 is a circuit schematic diagram of a gas sensor according to still another embodiment of the invention.

DESCRIPTION OF EMBODIMENTS

FIG. 1 is a circuit schematic diagram of a gas sensor according to an embodiment of the invention. Referring to FIG. 1, in the present embodiment, the gas sensor 100 includes a first sensing component 110, a second sensing component 120 and a voltage enhancement circuit 130. The first sensing component 110 is coupled between a first voltage V1 and a first node N1, where an impedance value of the first sensing component 110 is proportional to a gas concentration of a tested gas in the air. Namely, the lower gas concentration of the tested gas would result the lower impedance value of the first sensing component 110; and the higher gas concentration of the tested gas would result the higher impedance value of the first sensing component 110, where the tested gas can be filtered through a gas separation system, or the first sensing component 110 selects a specific material, which is known by those skilled in the art and not limited by the invention.

The second sensing component 120 is coupled between a second voltage V2 and the first node N1, where an impedance value of the second sensing component 120 is inversely proportional to the gas concentration of the tested gas in the air. Namely, the lower gas concentration of the tested gas would result the higher impedance value of the second sensing component 120; and the higher gas concentration of the tested gas would result, the lower impedance value of the second sensing component 120.

The voltage enhancement circuit 130 is coupled to the first node N1 to receive a node voltage Vn provided by the first node N1, and correspondingly provides a gas sensing voltage VGS, where the gas sensing voltage VGS relates to the node voltage Vn. For example, the gas sensing voltage VGS is equal to X times of the node voltage Vn, the gas sensing voltage VGS is proportional to the node voltage Vn, or the gas sensing voltage VGS is inversely proportional to the node voltage Vn, which are examples, and the invention is not limited thereto.

In the present embodiment, the first voltage V1 is different from the second voltage V2, for example, the first voltage V1 and the second voltage V2 can be respectively a system voltage and a ground voltage, the first voltage V1 can be greater than the second voltage V2, or the second voltage V2 is greater than the first voltage V1. When the first voltage V1 is greater than the second voltage V2, the node voltage Vn is inversely proportional to the gas concentration of the tested gas; when the second voltage V2 is greater than the first voltage V1, the node voltage Vn is proportional to the gas concentration of the tested gas.

In the embodiment of the invention, the first sensing component 110 and the second sensing component 120 can be packaged components, or can be electrodes (or materials) printed on the substrate, which is determined according to a circuit design, and is not limited by the invention.

FIG. 2 is a circuit schematic diagram of a gas sensor according to another embodiment of the invention. Referring to FIG. 1 and FIG. 2, the gas sensor 200 is substantially the same to the gas sensor 100, and a difference there lies in a voltage enhancement circuit 230 of the gas sensor 200, where the same or similar components are denoted by the same or similar referential numbers. In the present embodiment, the voltage enhancement circuit 230 includes a voltage amplifier VAMP1. An input terminal of the voltage amplifier VAMP1 is coupled to the first node N1 for receiving the node voltage Vn, and an output terminal of the voltage amplifier VAMP1 provides the gas sensing voltage VGS, where an amplification factor of the voltage amplifier VAMP1 is greater than or equal to 1. When the amplification factor of the voltage amplifier VAMP1 is equal to 1, the voltage amplifier VAMP1 can be regarded as a voltage follower; and when the amplification factor of the voltage amplifier VAMP1 is greater than 1, the voltage amplifier VAMP1 may amplify the node voltage Vn for providing the gas sensing voltage VGS, i.e. a variation of the gas sensing voltage VGS relative to the gas concentration is enlarged.

FIG. 3 is a circuit schematic diagram of a gas sensor according to still another embodiment of the invention. Referring to FIG. 1 and FIG. 3, the gas sensor 300 is substantially the same to the gas sensor 100, and a difference there lies in a voltage enhancement circuit 330 of the gas sensor 300, where the same or similar components are denoted by the same or similar referential numbers. In the present embodiment, the voltage enhancement circuit 330 includes a super diode DX1, a capacitor, a voltage follower VF1 and a differential amplifier DAMP1.

An input terminal of the super diode DX1 is coupled to the first node N1 for receiving the node voltage Vn. The capacitor C1 is coupled between an output terminal of the super diode DX1 and the ground voltage GND for providing a reference voltage VR. An input terminal of the voltage follower VF1 is coupled to the capacitor C1 for receiving the reference voltage VR, and an output terminal of the voltage follower VF1 is coupled to a negative input terminal of the differential amplifier DAMP1. A positive input terminal of the differential amplifier DAMP1 is coupled to the first node N1 for receiving the node voltage Vn, and a negative input terminal of the differential amplifier DAMP1 is coupled to the output terminal of the voltage follower VF1 for receiving the reference voltage VR, and an output terminal of the differential amplifier DAMP1 provides the gas sensing voltage VGS.

When the gas sensor 300 is in general air, i.e. no tested gas exists in the air, the capacitor C1 is charged to the highest voltage that can be reached by the node voltage Vn. When the tested gas enters the air, since the impedance values of the first sensing component 110 and the second sensing component 120 are changed, the node voltage Vn is varied, and now the super diode DX1 presents a reverse bias cut-off, so that a cross voltage of the capacitor C1 is maintained to the aforementioned highest voltage. Moreover, a difference between the highest voltage maintained by the capacitor C1 and a current voltage level of the node voltage Vn is amplified by the differential amplifier DAMP1 for providing the gas sensing voltage VGS, i.e. an intensity of a gas signal is further enhanced. The super diode DX1 is used for replacing a transistor switch, and used together with the capacitor C1 to form a circuit similar to a memory.

In the embodiment of the invention, since the voltage follower VF1 is used for separating the capacitor C1 and the differential amplifier DAMP1 for reducing a charge loss of the capacitor C1, though in case that a leakage current of the differential amplifier DAMP1 is extremely low, the voltage follower VF1 can be omitted without influencing the cross voltage of the capacitor C1, which can be determined according to an actual circuit design, and is not limited by the invention.

In summary, the gas sensor of embodiments of the invention push-pulls the node voltage of the first node according to the gas concentration through the first sensing component and the second sensing component connected in series and having positive and negative resistance coefficients, so that a variation amplitude of the node voltage can be increased relative to the gas concentration, i.e. sensing sensitivity for the gas concentration is improved. Moreover, the amplifier can be adopted to amplify the node voltage, so as to improve the variation amplitude of the gas sensing voltage, and further improve the sensing sensitivity of the gas sensor.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A gas sensor, comprising:
   a first sensing component, coupled between a first voltage and a first node, wherein an impedance value of the first sensing component is proportional to a gas concentration;
   a second sensing component, coupled between a second voltage and the first node, wherein an impedance value of the second sensing component is inversely proportional to the gas concentration; and
   a voltage enhancement circuit, coupled to the first node to receive a node voltage provided by the first node, and correspondingly providing a gas sensing voltage.

2. The gas sensor as claimed in claim 1, wherein the voltage enhancement circuit comprises:
   a voltage amplifier, having an input terminal coupled to the first node to receive the node voltage, and an output terminal providing the gas sensing voltage.

3. The gas sensor as claimed in claim 1, wherein the voltage enhancement circuit comprises:
   a differential amplifier, having a positive input terminal coupled to the first node to receive the node voltage, a negative input terminal receiving a reference voltage, and an output terminal providing the gas sensing voltage.

4. The gas sensor as claimed in claim 3, wherein the voltage enhancement circuit further comprises:
   a super diode, having an input terminal coupled to the first node to receive the node voltage and an output terminal; and
   a capacitor, coupled between the output terminal of the super diode and a ground voltage, and providing the reference voltage.

5. The gas sensor as claimed in claim 4, wherein the voltage enhancement circuit further comprises:
   a voltage follower, having an input terminal coupled to the capacitor to receive the reference voltage, and an output terminal coupled to the negative input terminal of the differential amplifier.

6. The gas sensor as claimed in claim 1, wherein the first voltage is greater than the second voltage.

7. The gas sensor as claimed in claim 1, wherein the second voltage is greater than the first voltage.

* * * * *